US00PP16601P2

(12) United States Plant Patent
McNaughton

(10) Patent No.: US PP16,601 P2
(45) Date of Patent: May 30, 2006

(54) *LAVANDULA* PLANT NAMED 'LAVANG 12'

(50) Latin Name: *Lavandula×chaytorae*
Varietal Denomination: Lavang 12

(76) Inventor: Virginia McNaughton, Lavender Downs, Lawford Road, West Melton, RD6, Christchurch (NZ)

( * ) Notice: Subject to any disclaimer, the term of this patent is extended or adjusted under 35 U.S.C. 154(b) by 102 days.

(21) Appl. No.: 10/949,754

(22) Filed: Sep. 25, 2004

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV ROM GTITM Computer Database, GTI Jouve Retrieval Software 2005/03 Citation for 'Lavang 12'.*

* cited by examiner

*Primary Examiner*—Kent Bell
*Assistant Examiner*—W. C. Haas

(57) ABSTRACT

A new cultivar of *Lavandula* plant named 'Lavang 12' that is characterized by long peduncle length, deep blue-violet spikes, large impressive habit and striking silver-grey foliage.

2 Drawing Sheets

Genus: *Lavandula.*
Species: ×*chaytorae.*
Denominatioan: 'Lavang 12'.

BACKGROUND OF THE INVENTION

The present invention, hereinafter referred to by the cultivar name 'Lavang 12', relates to a new and distinct cultivar of Lavender known botanically as *Lavandula×chaytorae* which (Upson and Andrews, "The Genus *Lavandula*", 2004, Royal Botanic Gardens, Kew, ISBN 1.84246.010.2) is a recently accepted new taxonomic designation for *Lavandula* hybrids arising from the interspecific cross *Lavandula angustifolia×Lavandula lanata.*

'Lavang 12' was selected by the inventor in 1995 in Canterbury, New Zealand, as a single flowering plant from a group of plants grown from seed resulting from the controlled hybridisation between *Lavandula angustifolia* 'Twickel Purple' (female parent, unpatented) and *Lavandula lanata* (male parent, unpatented). Thus, 'Lavang 12' is the result of hybridisation between two separate species, not between cultivars within a species.

'Lavang 12' is distinct and unique due to its silver-grey woolly foliage, large habit, deep blue-violet corollas and long spikes and peduncles.

'Lavang 12' is distinguishable from the parent plants in size, color of foliage, length of peduncle and color of spike. It is also much hardier than its *L. angustifolia* parent.

The inventor first asexually propagated 'Lavang 12' in 1995, using shoot cuttings taken from the single plant selected as above. Subsequent generations have been determined fixed, stable and true to type.

The inventor filed an application for grant of New Zealand Plant Breeders Rights on Jul. 7, 2003, Application Serial Number LAV038.

The first sale or supply of 'Lavang 12' was made by the inventor on Oct. 1, 2003, in New Zealand, under the trade name "Molten Silver".

SUMMARY OF THE INVENTION

The following traits have been repeatedly observed and represent the distinguishing characteristics of the new lavender cultivar 'Lavang 12'. These traits in combination distinguish 'Lavang 12' from all other known varieties of *Lavandula* known to the inventor. 'Lavang 12' has not been tested under all possible conditions and phenotype differences may be observed with variations in environmental, climatic, and cultural conditions, however, without any variance in genotype.

1. *Lavandula* 'Lavang 12' is a large growing lavender,of bushy and dense habit.
2. *Lavandula* 'Lavang 12' exhibits deep blue-violet corollas, long spikes, long peduncles and prolific branching pattern.
3. *Lavandula* 'Lavang 12' is the result of hybridsation between two separate species, not between cultivars within a species.
4. *Lavandula* 'Lavang 12' exhibits silver-grey foliage and the leaves have a velvety texture which is unusual in the Genus *Lavandula.*

BRIEF DESCRIPTION OF THE DRAWINGS

The accompanying color photographs illustrate the overall appearance of the new cultivar 'Lavang 12' showing colors as true as it is reasonably possible to obtain in colored reproductions of this type. Colors in the drawings may differ from the color values cited in the detailed botanical description, which accurately describe the actual colors of the new variety of 'Lavang 12'. The illustrated plants have been grown in open ground out-of-doors in Christchurch, New Zealand. No chemicals were used to treat the plants, which are 4-years-old.

The drawing labelled as FIG. 1 shows the entire plant from above and illustrating the spherical habit and long peduncles of 'Lavang 12'.

Figure 1:
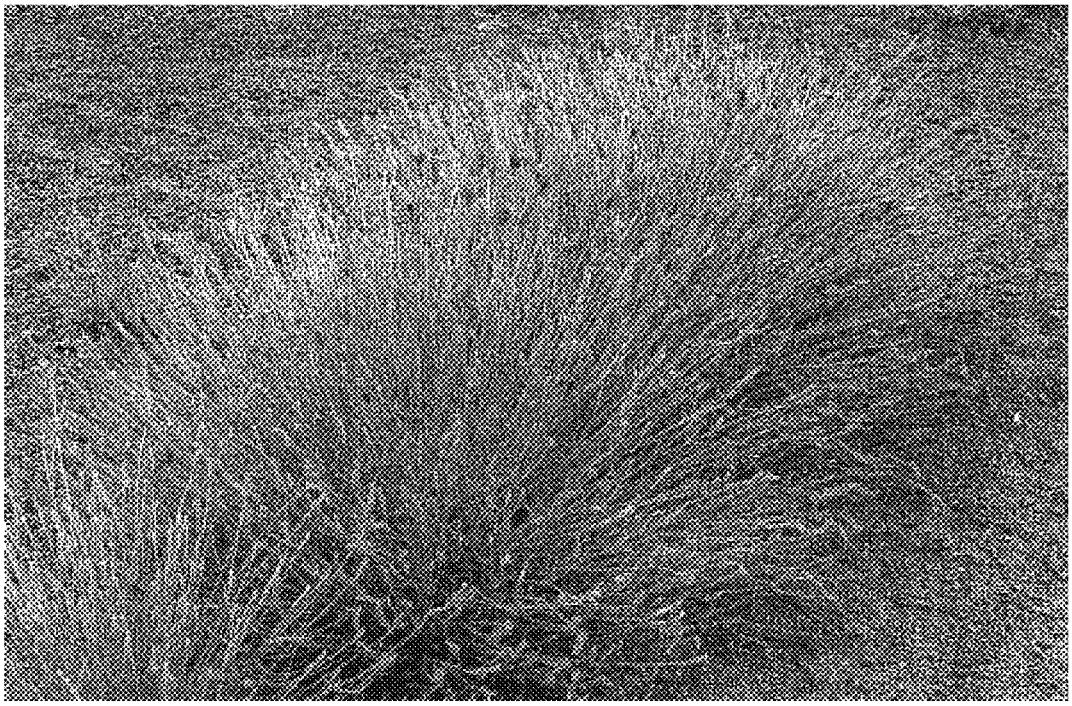
Figure 2:
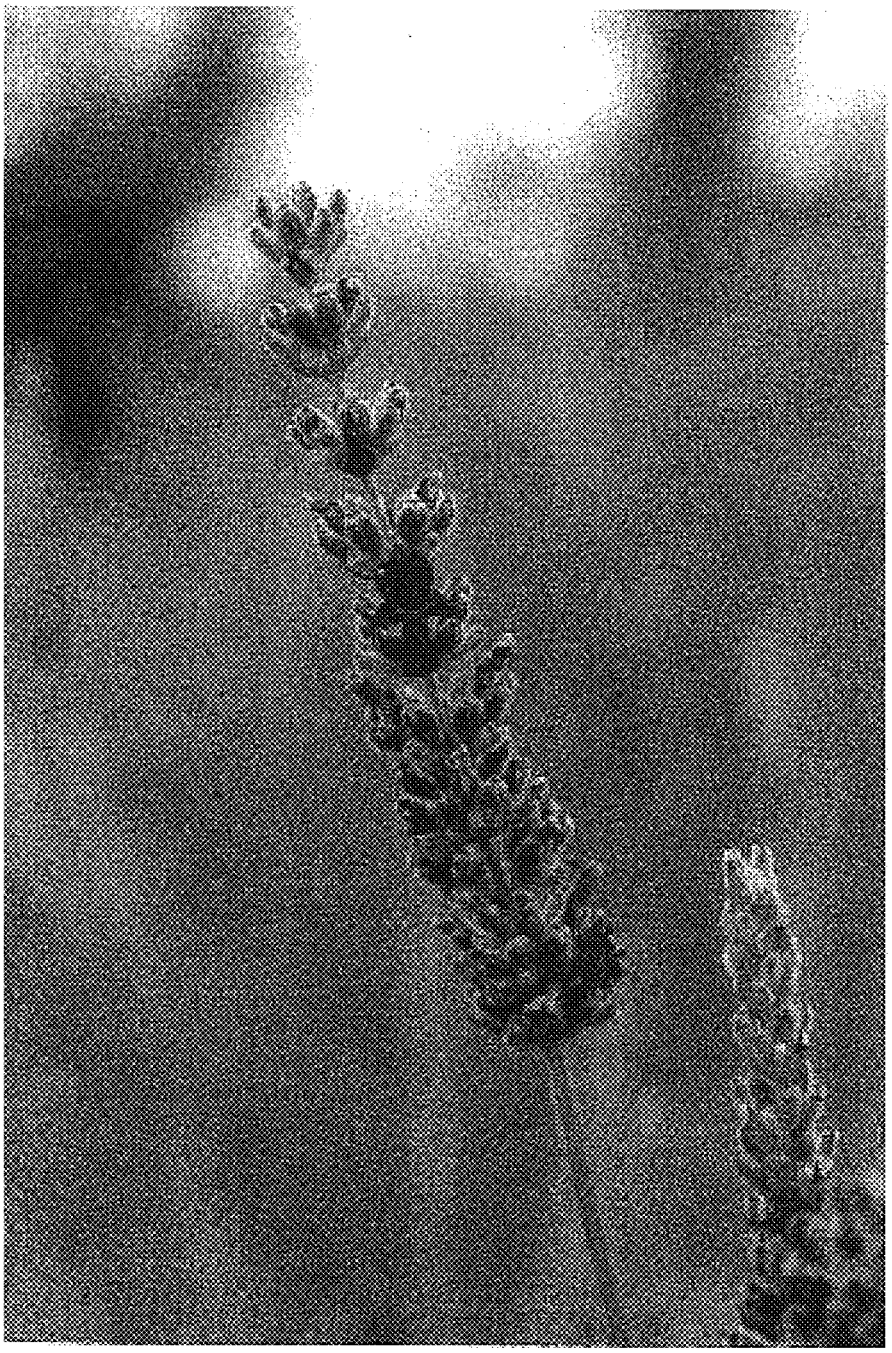

The drawing labelled as FIG. 2 shows a close up of a flower spike of 'Lavang 12'.

Both drawings are made using conventional photographic techniques and although foliage colors may appear different from actual colors due to light reflectance,they are as accurate as possible by conventional photography.

BOTANICAL DESCRIPTION OF THE PLANT

The following is a detailed description of the *Lavandula* cultivar named 'Lavang12'. Data was collected in West Melton, Canterbury, New Zealand from plants grown in the open ground. The plants are 4 year old and mature. No chemicals were used to treat the plants nor sprayed around them. Phenotypic differences may be observed with variation in environmental, climatic, and cultural conditions, without however, any difference in genotype.

Color determinations were conducted using a light box at The New Zealand Plant Variety Rights Office at Lincoln, Canterbury, New Zealand and were recorded by reference to the 2001 edition of Royal Horticultural Society (R.H.S.) Colour Chart, except where general color terms of ordinary dictionary significance are used. In certain instances, which are specified herein as applicable, a stated color match is the closest available. It appears that certain parts of Lavender plants and flowers present colors which are not exactly represented within the brown, green and violet ranges of the R.H.S. Colour Chart.

Botanical classification:
- *Genus.*—*Lavandula.*
- *Species.*—×*Chaytorae* (*Lavandula angustifolia*× *Lavandula lanata*).
- *Denomination.*—'Lavang 12'.

Common name: Lavender.

Parentage: 'Lavang 12' is the result of cross-pollination of the following parents:
- *Female parent plant.*—*Lavandula angustifolia* 'Twickel Purple' (unpatented).
- *Male parent plant.*—*Lavandula lanata* (unpatented).

Type: Aromatic perennial.

Use: Ornamental, feature, landscape, hedging or potted plant. Very effective grown en masse.

Growth rate: Moderate to vigorous.

Habit: Spherical with erect, ascending flower spikes.

Height: 70 cm to 1.0 m height.

Spread: 70 cm to 1.0 m in width.

Hardiness: Hardy to USDA Zone 5.

Propagation method: Cuttings root easily but difficult to initiate in tissue culture.

Root system: Fibrous.

Soil: Plant in well-drained soil.

Light levels: Plant in full sun.

Special needs: 'Lavang 12' benefits from pruning in autumn. Avoidance of water sitting on the soft velvet leaves (although 'Lavang 12' will survive in humid conditions as well as dry conditions.) Avoidance of over-watering at cutting stage or when growing in pots.

Time to initiate roots: 21 to 36 days are needed to develop roots on an unrooted cutting.

Time to develop 1-liter: 6 months are needed to produce a 1-liter container from a rooted cutting.

Branching habit: Foliage branched, erect and dense.

Seasonal interest: Silver grey, velvety foliage all year. Soft violet buds followed by deep blue-violet spikes from June through summer. Fairly tough plant in most respects. Very impressive as a feature plant in landscaping.

Stem:
- *Shape.*—Square.
- *Surface.*—Pubescent.
- *Color.*—Not exact match, ranges from 146A (yellow-green) to 177B (greyed-orange/brown).
- *Size.*—2 mm to 4 mm in diameter.

Foliage:
- *Arrangement.*—Upright stems with whorls of leaves, arranged opposite along stem. A basal pair of very long leaves subtend each whorl of smaller leaves. Dense arrangement of leaves along stems.
- *Leaf division.*—Simple.
- *Apices.*—Obtuse.
- *Base.*—Attenuate or truncate.
- *Margins.*—Entire and strongly revolute.
- *Leaf shape.*—Linear.
- *Color of mature leaves* (*upper surfaces*).—189B (grey-green), not exact match, looks silver-grey to naked eye.
- *Color of mature leaves* (*lower surfaces*).—189B (grey-green).
- *Color of young leaves* (*upper surfaces*).—188A (grey-green).
- *Color of young leave* (*lower surfaces*).—Too revolute to view.
- *Upper and lower surfaces.*—Densely pubescent.
- *Venation.*—Mid vein depressed on upper surface and protruding beneath, side veins impossible to see on lower surface.
- *Internodes.*—1.5 cm to 3.4 cm in length.
- *Foliar fragrance.*—Very different from other lavenders but has a slight camphoraceous and sweet scent combined. Very pleasant.
- *Petiole.*—Sessile.
- *Length of mature leaves.*—Approximately 2 cm to 5 cm in length.
- *Width of mature leaves.*—2 mm to 3 mm in width.

Flower:
- *Type of inflorescence.*—Terminal spike.
- *Size of infloresence.*—5 cm to 8 cm in length and 1 cm to 1.5 cm in width.
- *Shape of inflorescence.*—Tendency towards broad conical or cylindric and interrupted. Base whorl: 1 cm to 2 cm below main spike.
- *Peduncles.*—30–50 cm in length and 1 mm to 2 mm in width.
- *Peduncle position.*—Splayed outwards to give overall spherical effect.
- *Peduncle color.*—146A (dark yellow-green).
- *Lateral branches on peduncle.*—Frequent branching which is long, single or double, occasionally triple paired or one sided. Branches terminated with 2 to 6 flowers.
- *Flower shape.*—Tubular.
- *Corolla.*—Two-lipped with upper lip 2-lobed and lower lip 3-lobed.
- *Corolla color.*—88A (vibrant violet, not exact match).
- *Bud color.*—Pale 93A (dark violet blue with grey tinge, not exact match).
- *Calyx color.*—Similar to bud.
- *Calyx surface.*—Densely pubescent.
- *Bracteoles.*—Present, long and narrow or sometime broad.
- *Bracteole length.*—0.2 mm.

*Fertile bract size*.—Intermediate to broad and quite long, approximately 4 mm to 5 mm×4 mm to 5 mm or larger.

*Sterile bracts*.—Not present.

*Fragrance*.—Pleasant, somewhat camphoraceous, fragrance: highly uncharacteristic of the lavender genus.

*Oil content*.—High content of the following oils: linalool, octonone, lavandulyl acetate, lavandulol and terpinen-4-ol.

*Blooming period*.—June through summer.

Reproductive organs:

*Stamens*.—4.

*Stamen length* (*2 posterior*).—1 mm to 2 mm.

*Stamen length* (*2 anterior*).—0.5 mm to 1 mm.

*Pistil*.—1.

*Pistil length*.—5 mm to 7 mm.

*Pistil diameter*.—Less than 0.25 mm.

*Filament diameter*.—Less than 0.25 mm.

*Filament color*.—Grayish-white.

*Style length*.—4 mm–6 mm.

*Style color*.—Grayish-white.

*Stigma shape*.—Oval.

*Stigma color*.—Gray.

*Ovary shape*.—Oblong, globose.

*Ovary position*.—Superior.

*Ovary color*.—Green.

*Anther shape*.—Reniform.

*Anther length: Less than* 0.5 mm.

*Anther color*.—Brown.

*Polllen amount*.—Sparse.

*Pollen color*.—Yellow-orange.

Seed: Appears to be sterile.

It is claimed:

1. A new and distinct variety of *Lavandula* plant named 'Lavang 12' as described and illustrated.

* * * * *